(12) United States Patent
Kuroda et al.

(10) Patent No.: US 11,534,531 B2
(45) Date of Patent: Dec. 27, 2022

(54) CATHETER

(71) Applicant: KANEKA CORPORATION, Osaka (JP)

(72) Inventors: Keita Kuroda, Settsu (JP); Youhei Kurose, Settsu (JP)

(73) Assignee: KANEKA CORPORATION, Osaka (JP)

( * ) Notice: Subject to any disclaimer, the term of this patent is extended or adjusted under 35 U.S.C. 154(b) by 360 days.

(21) Appl. No.: 16/652,641

(22) PCT Filed: Dec. 4, 2018

(86) PCT No.: PCT/JP2018/044522
§ 371 (c)(1),
(2) Date: Mar. 31, 2020

(87) PCT Pub. No.: WO2019/124053
PCT Pub. Date: Jun. 27, 2019

(65) Prior Publication Data
US 2020/0237969 A1 Jul. 30, 2020

(30) Foreign Application Priority Data
Dec. 22, 2017 (JP) .............................. JP2017-246723

(51) Int. Cl.
*A61M 25/01* (2006.01)
*A61L 29/04* (2006.01)
(Continued)

(52) U.S. Cl.
CPC ............ *A61L 29/049* (2013.01); *A61M 5/007* (2013.01); *A61M 25/008* (2013.01);
(Continued)

(58) Field of Classification Search
CPC .......... A61M 25/0021; A61M 25/0045; A61M 25/0053; A61M 25/0054
See application file for complete search history.

(56) References Cited

U.S. PATENT DOCUMENTS

| 5,423,773 A | * | 6/1995 | Jimenez | ............ | A61M 25/0012 |
| | | | | | 604/526 |
| 6,030,369 A | * | 2/2000 | Engelson | .......... | A61M 25/0045 |
| | | | | | 604/525 |

(Continued)

FOREIGN PATENT DOCUMENTS

| JP | 2008-86470 A | 4/2008 |
| JP | 2008-104579 A | 5/2008 |

(Continued)

OTHER PUBLICATIONS

International Search Report for PCT/JP2018/044522 (PCT/ISA/210) dated Jan. 15, 2019.

(Continued)

*Primary Examiner* — Laura A Bouchelle
(74) *Attorney, Agent, or Firm* — Birch, Stewart, Kolasch & Birch, LLP

(57) ABSTRACT

A catheter (1) has a distal side and a proximal side and includes a tip part (10) and a main body part (20) disposed proximal to the tip part (10), the main body part (20) includes a first layer (21) and a second layer (22), the first layer (21) contains 60% by mass or more of an ethylene-tetrafluoroethylene copolymer, the second layer (22) is disposed inside of the first layer (21) in a radial direction of the catheter (1) and contains 60% by mass or more of a polyamide resin, and a cantilever bending load of the tip part (10) is smaller than a cantilever bending load of the main body part (20).

16 Claims, 2 Drawing Sheets

(51) Int. Cl.
  *A61M 5/00*   (2006.01)
  *A61M 25/00*  (2006.01)
(52) U.S. Cl.
  CPC .... *A61M 25/0045* (2013.01); *A61M 25/0108* (2013.01); *A61M 2210/1042* (2013.01)

(56) References Cited

U.S. PATENT DOCUMENTS

| | | | | |
|---|---|---|---|---|
| 6,451,005 | B1* | 9/2002 | Saitou | A61M 25/0053 |
| | | | | 604/526 |
| 8,387,347 | B2* | 3/2013 | Imai | A61L 29/041 |
| | | | | 604/93.01 |
| 9,913,933 | B2* | 3/2018 | Guo | A61M 25/0045 |
| 2012/0172840 | A1 | 7/2012 | Guo et al. | |
| 2014/0187964 | A1* | 7/2014 | Corl | A61B 8/4461 |
| | | | | 600/467 |
| 2020/0061352 | A1 | 2/2020 | Suzuki | |

FOREIGN PATENT DOCUMENTS

| | | |
|---|---|---|
| JP | 2012-196389 A | 10/2012 |
| JP | 2013-150747 A | 8/2013 |
| JP | 2014-50549 A | 3/2014 |
| JP | 2014-508560 A | 4/2014 |
| WO | WO 2018/212126 A1 | 11/2018 |

OTHER PUBLICATIONS

Written Opinion of the International Searching Authority for PCT/JP2018/044522 (PCT/ISA/237) dated Jan. 15, 2019.

* cited by examiner

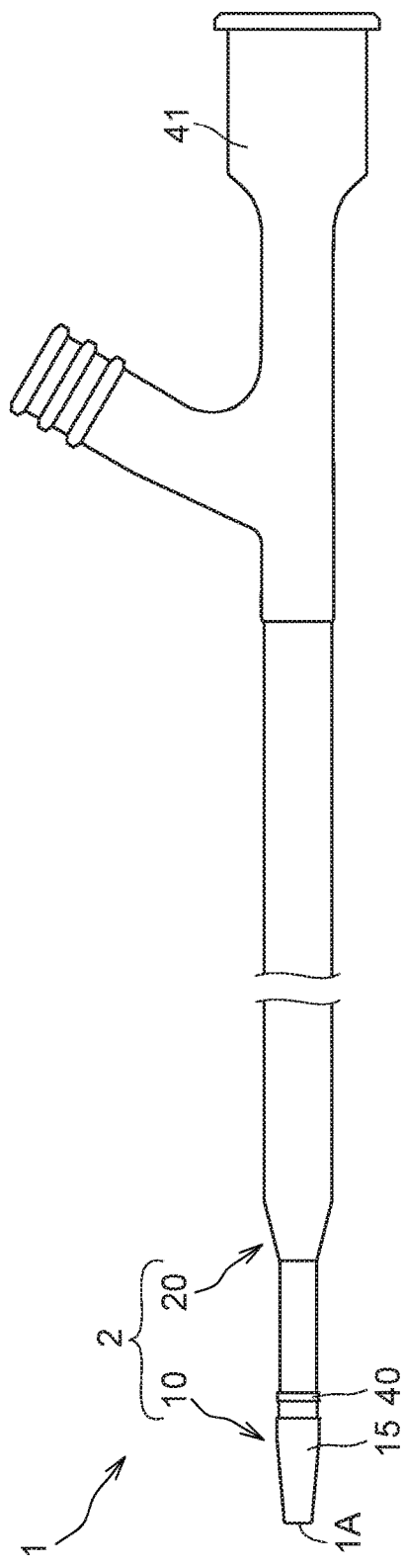
[Fig. 1]
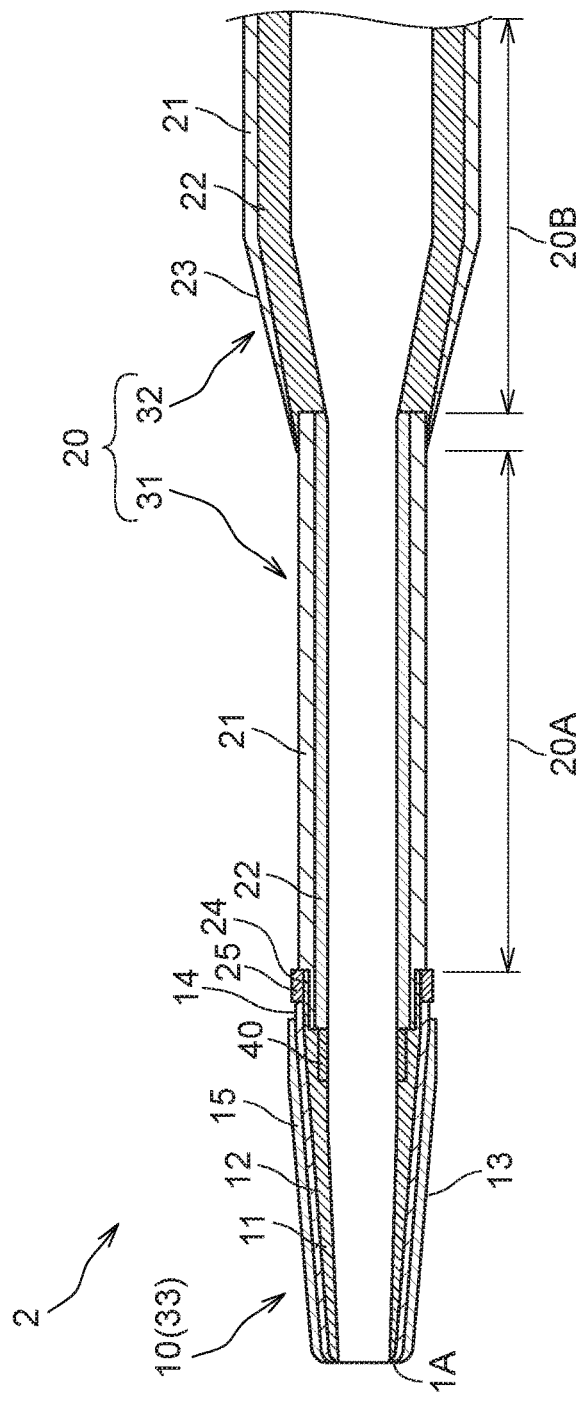
[Fig. 2]

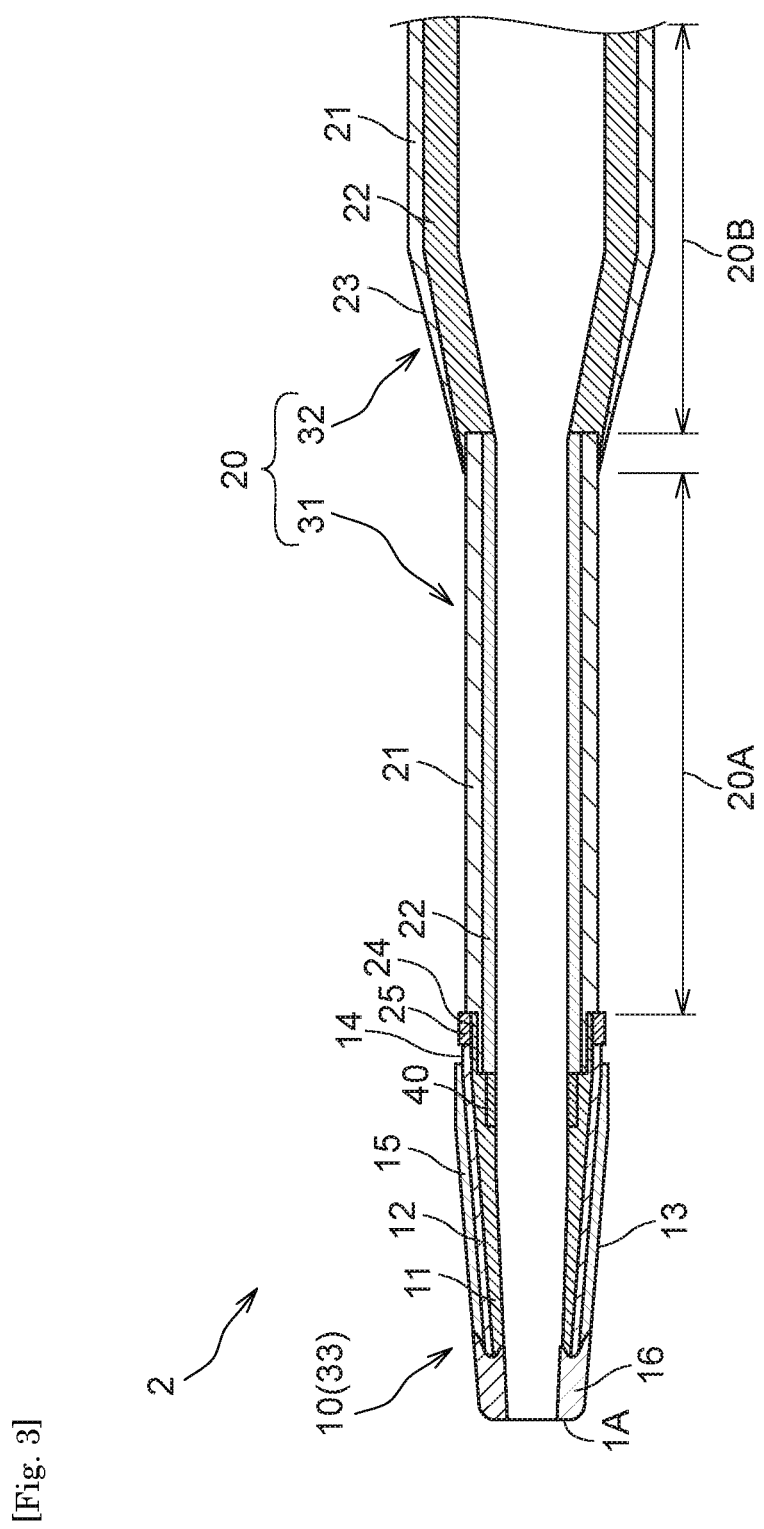
[Fig. 3]

CATHETER

TECHNICAL FIELD

The present invention relates to a catheter suitable for injecting a contrast medium into a living body.

BACKGROUND ART

In an endoscopic treatment of the digestive tract and blood vessels, the state of the inside of a target tract and lesions is checked by inserting a catheter into the target tract and injecting a contrast medium. For example, in a bile duct treatment using an intestinal endoscope, a catheter is inserted through a papilla in the duodenal wall into a bile duct, and a contrast medium is injected into the bile duct through the lumen of the catheter. A material which is easily plastically deformed, such as PTFE, is selected for the catheter used for contrast radiography so that the distal part of the catheter is bent in advance before being inserted into the lumen of the endoscope so as to allow the tip end of the catheter to protrude from the opening at the tip of the endoscope in a desired direction. However, a catheter made of PTFE may lack flexibility, and when the catheter is inserted into the papilla, the papilla may be stimulated due to contact with the distal end part of the catheter. In addition, since PTFE contains a chemically inert fluororesin, it has a problem of having difficulty bonding to other materials.

In view of this, multi-layered catheters that actively use materials other than PTFE have been developed. For example, Patent Document 1 discloses a catheter that includes a first polymer layer joined to a second polymer layer, and the second polymer layer includes an ethylene-perfluoro ethylene propylene ("EFEP") copolymer. Patent Document 1 also indicates that the first polymer layer preferably contains a reactive polar polymer, and that the EFEP copolymer preferably contains a functionalized EFEP copolymer and/or an end-functionalized copolymer.

PRIOR ART DOCUMENT

Patent Document

Patent Document 1: Japanese Unexamined Patent Application Publication (Translation of PCT Application) No. 2014-508560

SUMMARY OF THE INVENTION

Technical Problem

In the catheter disclosed in Patent Document 1, the reactive polar polymer contained in the first polymer layer and the end-functionalized EFEP copolymer contained in the second polymer layer provide excellent melt adhesion. However, due to insufficient flexibility at the distal part, the catheter may stimulate the living body during insertion, or slidability of a guide wire placed within the catheter may decrease. In view of this, an object of the present invention is to provide a catheter which can improve slidability of a member to be inserted in the lumen of the catheter, while ensuring flexibility of the tip part.

Solutions to the Problems

The gist of the present invention is as follows. A catheter according to the present invention that can overcome the above problems has a distal side and a proximal side and includes a tubular member having a tip part and a main body part disposed proximal to the tip part. The main body part includes a first layer and a second layer, the first layer contains 60% by mass or more of an ethylene-tetrafluoroethylene copolymer, the second layer is disposed inside of the first layer in a radial direction of the catheter and contains 60% by mass or more of a polyamide resin, and a cantilever bending load of the tip part is smaller than a cantilever bending load of the main body part. In the catheter according to the present invention, the first layer of the main body part of the tubular member is made of the above material, whereby the main body part can be easily bent in advance. Further, the second layer is made of the above material, whereby the slidability of the insertion member such as a guide wire can be improved while improving the adhesiveness with the first layer. In addition, the cantilever bending load of the main body part and the cantilever bending load of the tip part are different from each other, whereby the tip part can be made flexible.

Preferably, in the above catheter, the polyamide resin is at least one selected from the group consisting of nylon 12, nylon 11, and copolymer nylon combined thereof.

Preferably, in the above catheter, the tip part includes two or more layers laminated in the radial direction and does not include a layer containing an ethylene-tetrafluoroethylene copolymer.

Preferably, in the above catheter, the first layer and the second layer are directly joined to each other.

Preferably, in the above catheter, a third layer is disposed between the first layer and the second layer in the radial direction, and is made of a material different from materials of the first layer and the second layer.

Preferably, in the above catheter, the tip part has a tapered part, and an outer diameter of the tapered part decreases toward the distal side.

Preferably, in the above catheter, a radiopaque marker is disposed at a proximal end part of the tip part, and an outermost layer of the tip part is colored.

Preferably, in the above catheter, the radiopaque marker is disposed inside of the tip part in the radial direction.

Preferably, in the above catheter, the outermost layer of the tip part is made of a material containing a polyamide elastomer.

Preferably, in the above catheter, the main body part has a first section and a second section, the second section is positioned proximal to the first section and has a larger maximum outer diameter than the first section in a distal and proximal direction, and a three-point bending load in the first section is smaller than a three-point bending load in the second section.

Preferably, in the above catheter, the first layer is thicker than the second layer in the first section of the main body part, and the second layer is thicker than the first layer in the second section of the main body part.

Preferably, in the above catheter, a proximal part of the tip part includes an A layer and a B layer, the A layer contains 60% by mass or more of a polyamide resin, the B layer contains 60% by mass or more of a polyamide elastomer, and the B layer is disposed outside of the A layer in the radial direction.

Preferably, in the above catheter, an inner surface of the A layer at a proximal end part of the tip part is joined to an outer surface of the first layer at a distal end part of the main body part in the tubular member, a proximal end of the B layer is positioned distal to a proximal end of the A layer, and a colored layer is disposed on the distal end part of the main body part, on an outer side of the A layer in the radial direction, and proximal to the proximal end of the B layer.

Preferably, in the above catheter, a material constituting the A layer and a material constituting the B layer are mixed and melted at a distal part of the tip part.

Preferably, in the above catheter, the ethylene-tetrafluoroethylene copolymer is an ethylene-tetrafluoroethylene-hexafluoropropylene copolymer.

Preferably, in the above catheter, the ethylene-tetrafluoroethylene copolymer is a functionalized ethylene-tetrafluoroethylene copolymer into which a functional group is introduced.

Preferably, in the above catheter, the ethylene-tetrafluoroethylene copolymer is a functionalized ethylene-tetrafluoroethylene copolymer into which a functional group is introduced, and the introduced functional group is selected from the group consisting of a carbonate group, a carboxyl group, and a carbonyl group.

Advantageous Effects of the Invention

According to a catheter of the present invention, the main body part can be easily bent in advance, and the slidability of the insertion member such as a guide wire can be improved while improving the adhesiveness with the first layer. In addition, the cantilever bending load of the main body part and the cantilever bending load of the tip part are different from each other, whereby the tip part can be made flexible.

BRIEF DESCRIPTION OF DRAWINGS

FIG. 1 is a side view of a catheter according to an embodiment of the present invention.

FIG. 2 is an enlarged sectional view showing a distal side of the catheter shown in FIG. 1.

FIG. 3 is a modified example of the sectional view of the catheter shown in FIG. 2.

DESCRIPTION OF EMBODIMENTS

Hereinafter, the present invention will be specifically explained below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

1. Catheter

A catheter according to the present invention has a distal side and a proximal side and includes a tubular member having a tip part and a main body part disposed proximal to the tip part. The main body part includes a first layer and a second layer, the first layer contains 60% by mass or more of an ethylene-tetrafluoroethylene copolymer, the second layer is disposed inside of the first layer in a radial direction of the catheter and contains 60% by mass or more of a polyamide resin, and a cantilever bending load of the tip part is smaller than a cantilever bending load of the main body part. In the catheter according to the present invention, the first layer of the main body part of the tubular member is made of the above material, whereby the main body part can be easily bent in advance. Further, the second layer is made of the above material, whereby the slidability of the insertion member such as a guide wire can be improved while improving the adhesiveness with the first layer. In addition, the cantilever bending load of the main body part and the cantilever bending load of the tip part are different from each other, whereby the tip part can be made flexible.

In the present invention, the catheter refers to all medical catheters and includes balloon catheters, microcatheters, penetration catheters, and suction catheters. The catheter is preferably used for injecting a contrast medium in an examination (endoscopic retrograde cholangiopancreatography: ERCP) for imaging the bile duct and pancreatic duct with an endoscope. A proximal side of the catheter refers to a direction of a hand side of a user (operator) against an extension direction of the catheter, and the distal side refers to an opposite direction to the proximal side (that is, a direction of a treatment target side). In addition, a direction from the proximal side to the distal side of the catheter is referred to as an axial direction or a distal and proximal direction.

Hereinafter, the catheter according to an embodiment of the present invention is described by referring to FIGS. 1 to 3. FIG. 1 is a side view of a catheter according to an embodiment of the present invention. FIG. 2 is a cross-sectional view enlarged a distal side of a catheter shown in FIG. 1. FIG. 3 is a modified example of the cross-sectional view of the catheter shown in FIG. 2.

As shown in FIGS. 1 and 2, a catheter 1 according to an embodiment of the present invention has a distal side and a proximal side. A tubular member 2 of the catheter 1 has a tip part 10 and a main body part 20 disposed proximal to the tip part 10.

As shown in FIG. 2, both the tip part 10 and the main body part 20 are formed into a tubular shape having a lumen. The lumen of the tip part 10 and the lumen of the main body part 20 communicate with each other, and thus, a member such as a guide wire can be inserted into the catheter 1.

As shown in FIG. 2, the main body part 20 only needs to be disposed proximal to at least a part of the tip part 10, and is preferably disposed proximal to the center of the tip part 10 in the axial direction. As will be described later, the tip part 10 and the main body part 20 may be partly joined and overlapped with each other in the axial direction.

Since the cantilever bending load of the tip part 10 is smaller than the cantilever bending load of the main body part 20 in the catheter 1, the flexibility of the catheter 1 at the tip part 10 can be increased, and thus, stimulation caused when the catheter 1 passes through the papilla can be reduced, for example.

The cantilever bending loads of the tip part 10 and the main body part 20 are measured by the following procedure.
[Cantilever Bending Load Test]

(1) As a test piece, prepare at least five tubes (first test pieces) constituting at least a portion of the tip part 10 and at least five tubes (second test pieces) constituting at least a portion of the main body part 20. The length of each test piece in the axial direction is 70 mm.

(2) Fix one end of each test piece in the axial direction to the test piece holder of a bending tester.

(3) Measure the maximum load when each test piece is pushed 1 mm from top to bottom at a rate of 1 mm/min at a position 3 mm away from the fixed end.

(4) The average value of the loads of the first test pieces measured in the procedures (1) to (3) is defined as the cantilever bending load of the tip part 10, and the average value of the loads of the second test pieces is defined as the cantilever bending load of the main body part 20.

In step (1) of the cantilever bending load test, each test piece may be a tubular body before being assembled as the catheter 1, or may be a member obtained by cutting the catheter 1 along a direction perpendicular to the axial direction with a knife or the like.

In step (2) of the cantilever bending load test, a Shimadzu compact table-top testing machine EZ Test (EZ-SX) manufactured by Shimadzu Corporation can be used as a bending tester.

In step (2) of the cantilever bending load test, if the main body part 20 or the tip part 10 is provided with a tapered part that tapers toward the distal side, the side having no tapered part is fixed to the test piece holder.

The outer diameter of the tip part 10 can be set to 0.6 mm or more, 0.8 mm or more, or 1.0 mm or more, and can be set to 1.8 mm or less, 1.6 mm or less, or 1.4 mm or less, on the side proximal to the position 1 mm proximal to the distal end 1A of the catheter 1. The inner diameter of the tip part 10 can be set to 0.5 mm or more, 0.7 mm or more, or 1 mm or more, and can be set to 1.5 mm or less or 1.3 mm or less, on the side proximal to the position 1 mm proximal to the distal end 1A of the catheter 1. Note that a tapered part (second tapered part 13) to be described later is preferably provided on a side distal to the position 1 mm proximal to the distal end 1A of the catheter 1.

The tubular member 2 is made of a resin. The main body part 20 includes a first layer 21 and a second layer 22. The first layer 21 contains 60% by mass or more of an ethylene-tetrafluoroethylene copolymer. The second layer 22 is disposed inside of the first layer 21 in a radial direction of the catheter 1 and contains 60% by mass or more of a polyamide resin. In the catheter 1 according to the present invention, the first layer 21 of the main body part 20 of the tubular member 2 is made of the above material, whereby the main body part 20 can be easily bent in advance.

The ethylene-tetrafluoroethylene copolymer contains at least ethylene and tetrafluoroethylene as monomer units, and it is preferably an EFEP, ethylene-perfluoroethylene propylene, or ethylene-tetrafluoroethylene-hexafluoropropylene copolymer.

The ethylene-tetrafluoroethylene copolymer is preferably a functionalized ethylene-tetrafluoroethylene copolymer into which a functional group is introduced. Accordingly, the adhesiveness of the ethylene-tetrafluoroethylene copolymer is increased, and thus, the adhesiveness between the first layer and the second layer can be improved. The introduced functional group is preferably selected from the group consisting of a carbonate group, a carboxyl group, and a carbonyl group. The selected functional group preferably contains fluorine. Thus, slidability with the lumen of the endoscope can be improved.

The first layer 21 of the main body part 20 only needs to contain 60% by mass or more of the ethylene-tetrafluoroethylene copolymer. The content of the ethylene-tetrafluoroethylene copolymer in the first layer 21 is preferably 70% by mass or more, more preferably 80% by mass or more, still more preferably 90% by mass or more, and most preferably 95% by mass or more, and may also be 100% by mass or less or 98% by mass or less. If the content of the ethylene-tetrafluoroethylene copolymer is set in this manner, the main body part 20 can be more easily bent in advance, so that biostimulation during insertion of the catheter 1 can be suppressed. As the ethylene-tetrafluoroethylene copolymer, NEOFLON EFEP RP-5000 manufactured by Daikin Industries, Ltd. can be used, for example.

The second layer 22 of the main body part 20 only needs to contain 60% by mass or more of the polyamide resin. The content of the polyamide resin in the second layer 22 is preferably 70% by mass or more, more preferably 80% by mass or more, still more preferably 90% by mass or more, and most preferably 95% by mass or more, and may also be 100% by mass or less or 98% by mass or less. If the content of the polyamide resin is set in this manner, the adhesiveness between the first layer 21 and the second layer 22 is improved, and the slidability of the insertion member to be inserted into the lumen of the catheter 1, such as a guide wire, is improved.

In order to improve the adhesiveness between the first layer 21 and the second layer 22 and the slidability of the member to be inserted into the catheter 1, the polyamide resin is preferably at least one selected from the group consisting of nylon 12, nylon 11, and copolymer nylon obtained by combining nylon 11 and nylon 12. Specifically, for example, Rilsamid AESNO MED manufactured by Arkema Inc. can be used as the polyamide resin.

The material of the outer surface of the member to be inserted into the catheter 1 is preferably different from the material of the inner surface of the catheter 1. For example, when the surface of the member to be inserted into the catheter 1 is coated with a fluorine resin such as PTFE, the inner surface of the catheter 1 is preferably made of a material other than the fluorine resin.

As shown in FIGS. 1 and 2, the first layer 21 and the second layer 22 are preferably directly joined to each other. With this configuration, the second layer 22 containing 60% by mass or more of the polyamide resin easily bonds to the first layer 21 containing the ethylene-tetrafluoroethylene copolymer, so that the effect of preventing delamination of the first layer 21 can be increased. Examples of the method for directly joining the first layer 21 and the second layer 22 include thermal welding. Before the layers are directly joined, a surface modification treatment such as a plasma treatment or a corona treatment may be performed.

Although not shown, a third layer may be disposed between the first layer 21 and the second layer 22 in the radial direction, is made of a material different from materials of the first layer 21 and the second layer 22. In that case, the content of the polyamide resin in the third layer is preferably 60% by mass or more, more preferably 70% by mass or more, still more preferably 80% by mass or more, and most preferably 90% by mass or more, and may also be 100% by mass or less or 98% by mass or less. The third layer functions as an adhesive layer for joining the first layer 21 and the second layer 22. When the third layer is made of the material described above, the first layer 21 and the second layer 22 can be indirectly joined. Examples of the polyamide resin contained in the third layer include the abovementioned polyamide resins.

When the third layer is provided in the main body part 20, it is preferable that the third layer contains more polyamide resin than the second layer 22. When the content of the polyamide resin in the third layer is set as described above, the first layer 21 and the third layer can be appropriately bonded.

Each layer of the main body part 20 may contain polyamide resin different from the abovementioned polyamide resins, polyester resin, polyurethane resin, polyolefin resin, fluorine resin, vinyl chloride resin, silicone resin, natural rubber, etc. These materials may be used alone, or two or more of them may be used in combination.

The main body part 20 may have a constant outer diameter in the distal and proximal direction. Alternatively, it is preferable that the main body part 20 has a first section 20A and a second section 20B, the second section 20B being positioned proximal to the first section 20A and having a larger maximum outer diameter than the first section 20A in the distal and proximal direction. In that case, it is preferable that a three-point bending load in the first section 20A is smaller than a three-point bending load in the second section 20B. When the main body part 20 is provided with the first section 20A and the second section 20B as described above, the rigidity of the catheter 1 can be continuously changed. Note that, during the procedure, at least the distal part of the first section 20A is positioned distal to the distal end of the endoscope.

The outer diameter of the first section 20A can be set to 1 mm or more, 1.5 mm or more, or 2 mm or more, and can be set to 5 mm or less, 4 mm or less, or 3 mm or less. The inner diameter of the first section 20A can be set to 0.5 mm or more, 1 mm or more, or 1.5 mm or more, and can be set to 3 mm or less or 2 mm or less. The outer diameter of the second section 20B can be set to 1.5 mm or more, 2 mm or more, or 2.5 mm or more, and can be set to 6 mm or less, 5 mm or less, or 4 mm or less. The inner diameter of the second section 20B can be set to 1 mm or more, 1.5 mm or more, or 2 mm or more, and can be set to 4 mm or less or 3 mm or less.

In the present invention, the three-point bending loads are measured by the following procedure.

[Three-Point Ending Load Test]

(1) As a test piece, prepare at least five tubes (Third test pieces) constituting at least a portion of the first section 20A of the main body part 20 and at least five tubes (Fourth test pieces) constituting at least a portion of the second section 20B of the main body part 20. The length of each test piece in the axial direction is 100 mm.

(2) Fix both ends of each test piece in the axial direction to the test piece holder of a bending tester.

(3) Measure the maximum load when each test piece is pushed 1 mm from top to bottom at a rate of 5 mm/min at a central position of the two fixed ends.

(4) The average value of the loads of the third test pieces measured in the procedures (1) to (3) is defined as the three-point bending load of the first section 20A, and the average value of the loads of the fourth test pieces is defined as the three-point bending load of the second section 20B.

In step (1) of the three-point bending load test, each test piece may be a tubular body before being assembled as the catheter 1, or may be a member obtained by cutting the catheter 1 along a direction perpendicular to the axial direction with a knife or the like.

The other procedures of the three-point bending load test can be performed in the same manner as the cantilever bending load test.

The second section 20B is preferably longer than the first section 20A in the axial direction. The length of the second section 20B can be set to, for example, 1800 mm or more and 2400 mm or less, and the length of the first section 20A can be set to, for example, 50 mm or more and 300 mm or less.

The distal end part of the second section 20B preferably has a tapered part 23 (hereinafter, referred to as "first tapered part 23"), and an outer diameter of the first tapered part 23 decreases toward the distal side. Due to the first tapered part 23 being formed as described above, the degree of a change in rigidity of the main body part 20 can be adjusted. The first tapered part 23 is more preferably formed in a conical shape.

Preferably, the first layer 21 is thicker than the second layer 22 in the first section 20A of the main body part 20, and the second layer 22 is thicker than the first layer 21 in the second section 20B of the main body part 20. Specifically, in the first section 20A of the main body part 20, the thickness ratio between the first layer 21 and the second layer 22 (first layer 21: second layer 22) is preferably 9:1 to 6:4. In the second section 20B, the thickness ratio between the first layer 21 and the second layer 22 is preferably 1:9 to 4:6. By setting the thickness of the first section 20A and the second section 20B of the main body part 20 as described above, the rigidity of the catheter 1 can be continuously changed in the axial direction. Here, the thickness of the first layer 21 and the second layer 22 indicates the maximum thickness.

At the distal end part of the second section 20B, the thickness of the first layer 21 may increase toward the distal side. Since the ethylene-tetrafluoroethylene copolymer in the first layer 21 has lower rigidity than the polyamide in the second layer 22, the difference in rigidity between the first section 20A and the second section 20B can be reduced by setting the thickness of the first layer 21 as described above. When the third layer is provided in the main body part 20, the first layer 21, the second layer 22, and the third layer may have a constant thickness in the axial direction or may vary in thickness in the axial direction.

The main body part 20 can be formed by connecting, in the axial direction, a first tubular member 31 having the first layer 21 and the second layer 22 and a second tubular member 32 which has a larger maximum outer diameter than the first tubular member 31 and which has the first layer 21 and the second layer 22. In that case, it is preferable that the proximal end part of the first tubular member 31 is inserted into the lumen at the distal end part of the second tubular member 32. It is preferable that the first tubular member 31 and the second tubular member 32 are welded or bonded to each other.

More preferably, the outer surface and the proximal end surface of the first tubular member 31 at the proximal end part are in contact with the inner layer (second layer 22 in FIG. 2) of the second tubular member 32. In that case, it is preferable that an outermost layer (the first layer 21 in FIG. 2) of the second tubular member 32 is not in contact with the first tubular member 31. Since the second layer 22 of the second tubular member 32 functions as an adhesive layer with the first layer 21 of the first tubular member 31, delamination of each layer in the first tubular member 31 can be prevented.

The tip part 10 is provided in an area including the distal end 1A of the catheter 1. The length of the tip part 10 in the axial direction can be set to, for example, 20 mm or less, 15 mm or less, or 10 mm or less, and may be set to 2 mm or more or 3 mm or more, on the distal side from the distal end of the first section 20A. The tip part 10 is preferably formed shorter in the axial direction than the main body part 20, for example, the length of the tip part 10 is 1/200 or less, 1/150 or less, or 1/100 or less of the length of the main body part 20.

The tip part 10 may be composed of a single layer or may have two or more layers laminated in the radial direction. A portion of the tip part 10 in the axial direction or the circumferential direction may be composed of a single layer, and another portion may be composed of two or more layers. For example, as shown in FIG. 2, the tip part 10 may include an A layer 11 and a B layer 12 disposed outside of the A layer 11 in the radial direction. Due to the configuration in which at least a portion of the tip part 10 in the axial direction has a multilayer structure as described above, the adhesiveness with the main body part 20 can be increased with the flexibility of the tip part 10 being ensured.

The content of a polyamide resin in the A layer 11 of the tip part 10 is preferably 60% by mass or more, more preferably 70% by mass or more, further preferably 80% by mass or more, still more preferably 90% by mass or more, and most preferably 95% by mass or more, and may also be 100% by mass or less or 98% by mass or less. When the A layer 11 contains a certain amount of the polyamide resin, the resistance of the insertion member such as the guide wire can be reduced. As a material constituting the A layer 11, for example, Rilsamid AESNO MED manufactured by Arkema Inc. can be used.

The content of a polyamide elastomer in the B layer 12 of the tip part 10 is preferably 60% by mass or more, more preferably 70% by mass or more, further preferably 80% by mass or more, still more preferably 90% by mass or more, and most preferably 95% by mass or more, and may also be 100% by mass or less or 98% by mass or less. When the B layer 12 contains a certain amount of the polyamide elastomer as described above, the flexibility increases on the outer side of the tip part 10 in the radial direction, whereby stimulation caused when the tip part 10 contacts the living body can be reduced. As a material constituting the B layer 12, for example, PEBAX5533 manufactured by Arkema Inc. can be used.

It is preferable that the tip part 10 includes two or more layers laminated in the radial direction and does not include a layer containing an ethylene-tetrafluoroethylene copolymer. When a layer containing an ethylene-tetrafluoroethylene copolymer is not provided to the tip part 10, the flexibility of the tip part 10 can be further enhanced.

In general, during manufacture of the catheter 1, the distal end part is processed into a tapered shape by inserting a tubular body that is the base of the catheter into a hollow mold. During such process, a sharp burr may be generated on the distal end part. The burr is preferably removed by cutting or melting, because it may damage or stimulate the living body.

When the burr is cut during the manufacture of the catheter 1, a distal part of the tip part 10 of the catheter 1 has a multilayer structure as shown in FIG. 2. For example, the A layer 11 containing 60% by mass or more of a polyamide resin and the B layer 12 disposed outside of the A layer 11 in the radial direction and containing 60% by mass or more of a polyamide elastomer may be provided on the distal part of the tip part 10. The flexibility of the tip part 10 can be increased by configuring the tip part 10 as described above.

As shown in FIG. 3, the material constituting the A layer 11 and the material constituting the B layer 12 may be mixed and melted on the distal part of the tip part 10 of the catheter 1 by melting the burr during the manufacture of the catheter 1. FIG. 3 shows that a mixed layer 16 is formed by mixing and melting the materials constituting the A layer 11 and the B layer 12 on the distal part of the tip part 10. When the distal part of the tip part 10 is configured as described above, the stimulation caused when the tip part 10 contacts the living body can be reduced, and delamination of each layer on the distal end part of the tubular member 2 can be prevented.

It is preferable that the proximal part of the tip part 10 includes the A layer 11 and the B layer 12, the A layer 11 contains 60% by mass or more of a polyamide resin, the B layer 12 contains 60% by mass or more of the polyamide elastomer, and the B layer 12 is disposed outside of the A layer 11 in the radial direction. The flexibility of the tip part 10 can be increased by the B layer 12 containing the polyamide elastomer. Further, since the A layer 11 containing the polyamide resin is easily bonded to the first layer 21 of the main body part 20, the tip part 10 and the main body part 20 can be reliably connected to each other.

An outermost layer of the tip part 10 is preferably made of a material containing a polyamide elastomer. As a result, the flexibility of the tip part 10 can be increased, so that the stimulation caused when the tip part 10 contacts the living body is further reduced.

The tip part 10 preferably has a tapered part (hereinafter, referred to as "second tapered part 13"), and an outer diameter of the second tapered part 13 decreases toward the distal side. More preferably, the second tapered part 13 is provided at a position including the distal end of the tip part 10. When the second tapered part 13 is provided as described above, the flexibility of the tip part 10 increases toward the distal side, so that the catheter 1 is less likely to stimulate the living body.

The tip part 10 and the main body part 20 may be connected by connecting two tubular members. For example, it is preferable that the proximal part of a third tubular member 33 constituting the tip part 10 and the tubular member constituting the main body part 20 (more preferably, the distal part of the first tubular member 31 described above) are connected to each other. In that case, it is preferable that the distal end part of the first tubular member 31 is inserted into the lumen of the third tubular member 33 at the proximal end part. The tip part 10 and the main body part 20 can be joined to each other by bonding or welding. The tip part 10 and the main body part 20 are preferably joined to each other by thermal welding.

As shown in FIGS. 2 and 3, a thin part 24 in which the total thickness of the first layer 21 and the second layer 22 is smaller than that at the proximal end part of the first section 20A is preferably formed at the distal end part of the main body part 20. In that case, it is preferable that the outer surface of the thin part 24 and the inner surface of the proximal end part of the tip part 10 are joined. When the thin part 24 is provided as described above, the outer diameter of the tubular member 2 at the joint portion between the tip part 10 and the main body part 20 can be reduced. At the distal end part (more preferably, the thin part 24) of the main body part 20, the outer surface of the first layer 21 and the inner surface of the A layer 11 of the tip part 10 (more preferably, the inner surface of the A layer 11) are in contact with each other. In that case, the A layer 11 preferably contains 60% by mass or more of the polyamide resin. Due to the configuration in which the tip part 10 and the main body part 20 are connected to each other as described above, the A layer 11 functions as a bonding layer between the first layer 21 of the main body part 20 and the B layer 12 of the tip part 10, whereby delamination of the B layer 12 of the tip part 10 from the first layer 21 of the main body part 20 can be prevented.

Similar to the main body part 20, a thin part 14 having a total thickness smaller than that at the distal end of the tip part 10 may be provided at the proximal end part of the tip part 10. In that case, it is preferable that the thin part 14 of the tip part 10 and the thin part 24 of the main body part 20 are joined to each other. Accordingly, it is possible to suppress an increase in the outer diameter of the tubular member 2 at the joint portion between the tip part 10 and the main body part 20.

In order to visually recognize the insertion position in the body, the catheter 1 may be provided with a radiopaque marker 40 or a colored layer described below.

The radiopaque marker is preferably disposed at the proximal end part of the tip part 10. When the radiopaque marker 40 is disposed as described above, the position of the tip part 10 can be easily recognized under radioscopy.

Preferably, the radiopaque marker 40 is disposed inside of the tip part 10 in the radial direction, and more preferably, it is disposed on the innermost part of the tip part 10 in the radial direction. When the radiopaque marker 40 is disposed as described above, the rigidity of the tip part 10 is less likely to increase.

The shape of the radiopaque marker 40 is not particularly limited, but is preferably tubular, and examples of the shape include a cylindrical shape, a polygonal tube shape, a shape with a C-shaped cross section obtained by forming a slit in a tube, and a coil shape obtained by winding a wire material.

The material constituting the radiopaque marker 40 is not particularly limited. For example, a metal material such as stainless steel, titanium, cobalt chromium alloy, or platinum iridium alloy can be used.

The tip part 10 may has a colored layer (hereinafter, referred to "first colored layer 15") disposed outside of the B layer 12 in the radial direction. In that case, the first colored layer 15 is preferably disposed on the outermost side of the tip part 10. That is, the outermost layer of the tip part 10 may be colored. Thus, when the catheter 1 is inserted into the living body lumen, the position of the tip part 10 can be easily visually recognized by the endoscope. [0080]

In order to make it easy to visually recognize the position of the tip part 10 under radioscopy and with an endoscope, it is preferable that the radiopaque marker 40 is disposed at the proximal end part of the tip part 10, and that the outermost layer of the tip part 10 is colored.

More preferably, the first colored layer 15 is made of a material containing a polyamide elastomer and a colorant. The colorant preferably contains a pigment. In that case, it is preferable that the B layer 12 and the first colored layer 15 of the tip part 10 are different in color. Being different in color means that at least one of hue, brightness, and saturation defined in JIS Z8721 is different. For example, the B layer 12 can be made transparent, and the first colored layer 15 can be colored in black. By making the B layer 12 transparent, the state of the member passing through the lumen of the tubular member 2 can be observed with the camera of the endoscope. The first colored layer 15 preferably has a color, such as black, which hardly transmits light from a light source of the endoscope and by which the difference in color from the wall of the body cavity is easy to be observed. In order to make it difficult to transmit light, the first colored layer 15 can also be formed by mixing a white pigment that does not easily transmit light.

Preferably, a colored layer (hereinafter referred to "second colored layer 25") is disposed at a distal end part of the main body part 20. Thus, when the catheter 1 is inserted into the living body lumen, the position of the tip part 10 can be easily visually recognized by the endoscope. In order to suppress an increase in the outer diameter of the tubular member 2, the second colored layer 25 may be provided on the thin part 24 of the main body part 20.

The second colored layer 25 is preferably disposed on an outermost layer of the main body part 20. Thus, the tip part 10 can be further easily visually recognized by the endoscope.

It is preferable that, when the proximal part of the tip part 10 has the A layer 11 and the B layer 12, and the inner surface of the A layer 11 at a proximal end part of the tip part 10 is joined to an outer surface of the first layer 21 at a distal end part of the main body part 20 in the tubular member 2, a proximal end of the B layer 12 is positioned distal to a proximal end of the A layer 11, and a colored layer (second colored layer 25) is disposed on the distal end part of the main body part 20, outside of the A layer 11 in the radial direction, and proximal to the proximal end of the B layer 12. In that case, it is more preferable that the B layer 12 of the tip part 10 and the first layer 21 of the main body part 20 are not in contact with each other. The configuration in which the second colored layer 25 is disposed as described above can prevent direct contact between the B layer 12 of the tip part 10 preferably composed of a material containing a polyamide elastomer and the first layer 21 of the main body part 20 containing 60% by mass or more of an ethylene-tetrafluoroethylene copolymer, whereby delamination of the B layer 12 of the tip part 10 from the first layer 21 of the main body part 20 can be prevented.

The content of a polyamide resin in the second colored layer 25 is preferably 60% by mass or more, more preferably 70% by mass or more, further preferably 80% by mass or more, still more preferably 90% by mass or more, and most preferably 95% by mass or more, and may also be 100% by mass or less or 98% by mass or less. When the second colored layer 25 is made of the abovementioned material, bondability between the layer (B layer 12) containing the polyamide elastomer in the tip part 10 and the second colored layer 25 is improved.

The second colored layer 25 is preferably made of a material containing a polyamide resin and a colorant. The colorant preferably contains a pigment. In that case, the second colored layer 25 and the first layer 21 are preferably different in color in order to make it easy to visually recognize the position of the tip part 10.

It is preferable that the first colored layer 15 and the second colored layer 25 are different in color. This makes it easy to accurately recognize the insertion position of the catheter 1.

When the thin part 24 is provided at the distal end part of the main body part 20, the second colored layer 25 is preferably provided outside of the thin part 24 in the radial direction. In that case, it is more preferable that the B layer 12 of the tip part 10 and the second colored layer 25 of the main body part 20 are joined to each other, and that the proximal end surface of the B layer 12 and the distal end surface of the second colored layer 25 are joined to each other. The configuration in which the second colored layer 25 is disposed as described above can prevent direct contact between the B layer 12 of the tip part 10 preferably composed of a material containing a polyamide elastomer and the first layer 21 of the main body part 20 containing 60% by mass or more of an ethylene-tetrafluoroethylene copolymer, whereby delamination of the B layer 12 of the tip part 10 from the first layer 21 of the main body part 20 can be further prevented.

In order to enable manipulation by hand, it is preferable that a manifold 41 having a lumen and extending in the distal and proximal direction is connected to the proximal end part of the main body part 20 as shown in FIG. 1. The manifold 41 is connected with a syringe or the like for injecting a contrast medium or a drug into the tip part 10 and the main body part 20. The shape and structure of the manifold 41 are not particularly limited, and known ones can be used.

This application claims priority to Japanese Patent Application No. 2017-246723, filed on Dec. 22, 2017, and Japanese Patent Application No. 2017-246723, filed on Dec. 22, 2017, and the entire contents of which are incorporated by reference herein.

REFERENCE SIGNS LIST

1: a catheter
1A: a distal end
2: a tubular member
10: a tip part
11: an A layer
12: a B layer
13: a second tapered part
14: a thin part
15: a first colored layer
16: a mixed layer
20: a main body part
20A: a first section
20B: a second section
021: a first layer
22: a second layer
23: a first tapered part
24: a thin part
25: a second colored layer
31: a first tubular member
32: a second tubular member
33: a third tubular member
40: a radiopaque marker
41: a manifold

The invention claimed is:

1. A catheter having a distal side and a proximal side, comprising:
a tip part located at the distal side of the catheter; and
a main body part located at the proximal side of the catheter, the main body part and the tip part connected to each other to form a tubular member, wherein
the main body part includes a first layer and a second layer,
the first layer contains 60% by mass or more of an ethylene-tetrafluoroethylene copolymer,
the second layer is disposed inside of the first layer in a radial direction of the catheter and contains 60% by mass or more of a polyamide resin,
a cantilever bending load of the tip part is smaller than a cantilever bending load of the main body part at a cantilever bending load test,
a radiopaque marker is disposed at a proximal end part of the tip part,
an outermost layer of the tip part is colored, so that position of the tip part can be visually recognized by an endoscope when the catheter is inserted into a body lumen, and
the radiopaque marker is positioned so as to expose to a lumen of the tip part.

2. The catheter according to claim 1, wherein
the polyamide resin comprises at least one resin selected from the group consisting of nylon 12, nylon 11, and copolymer nylon combined thereof.

3. The catheter according to claim 1, wherein
the tip part includes two or more layers laminated in the radial direction and does not include a layer containing an ethylene-tetrafluoroethylene copolymer.

4. The catheter according to claim 1, wherein
the first layer and the second layer are directly joined to each other.

5. The catheter according to claim 1, wherein
a third layer is disposed between the first layer and the second layer in the radial direction, and is made of a material different from materials of the first layer and the second layer.

6. The catheter according to claim 1, wherein
the tip part has a tapered part, and an outer diameter of the tapered part decreases toward the distal side.

7. The catheter according to claim 1, wherein
the outermost layer of the tip part comprises a polyamide elastomer.

8. The catheter according to claim 1, wherein
the main body part has a first section and a second section in a distal and proximal direction,
the second section is positioned proximal to the first section and has a larger maximum outer diameter than the first section, and
a three-point bending load in the first section is smaller than a three-point bending load in the second section at a three-point bending load test.

9. The catheter according to claim 8, wherein
the first layer is thicker than the second layer in the first section of the main body part, and
the second layer is thicker than the first layer in the second section of the main body part.

10. The catheter according to claim 1, wherein
a proximal part of the tip part includes an A layer and a B layer, the A layer contains 60% by mass or more of a polyamide resin, the B layer contains 60% by mass or more of a polyamide elastomer, and the B layer is disposed outside of the A layer in the radial direction.

11. The catheter according to claim 10, wherein
an inner surface of the A layer at a proximal end part of the tip part is joined to an outer surface of the first layer at a distal end part of the main body part in the tubular member,
a proximal end of the B layer is positioned distal to a proximal end of the A layer, and
a colored layer is disposed on the distal end part of the main body part, on an outer side of the A layer in the radial direction, and proximal to the proximal end of the B layer.

12. The catheter according to claim 10, wherein
a material constituting the A layer and a material constituting the B layer are melted together to form a distal end part of the tip part.

13. The catheter according to claim 1, wherein
the ethylene-tetrafluoroethylene copolymer is an ethylene-tetrafluoroethylene-hexafluoropropylene copolymer.

14. The catheter according to claim 1, wherein
the ethylene-tetrafluoroethylene copolymer is a functionalized ethylene-tetrafluoroethylene copolymer into which a functional group is introduced.

15. The catheter according to claim 1, wherein
the ethylene-tetrafluoroethylene copolymer is a functionalized ethylene-tetrafluoroethylene copolymer into which a functional group is introduced, and
the introduced functional group is selected from the group consisting of a carbonate group, a carboxyl group, and a carbonyl group.

16. The catheter according to claim 1, wherein
the main body part has a first section and a second section in a distal and proximal direction, and
the second section is positioned proximal to the first section and has a larger maximum outer diameter than the first section.

* * * * *